United States Patent
Ni et al.

(10) Patent No.: US 8,748,115 B2
(45) Date of Patent: Jun. 10, 2014

(54) PCSK9 IMMUNOASSAY

(75) Inventors: Yan Ni, Westfield, NJ (US); Ayesha Sitlani, Metuchen, NJ (US); Shilpa Pandit, Edison, NJ (US); Dale Lewis, Washington Crossing, PA (US); Xun Shen, Piscataway, NJ (US); Sharon Lobo, Hackettstown, NJ (US); Timothy McCabe, Doylestown, PA (US); Jon Condra, Doylestown, PA (US); Rose Cubbon, Fanwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 340 days.

(21) Appl. No.: 13/139,045

(22) PCT Filed: Dec. 2, 2009

(86) PCT No.: PCT/US2009/066303
§ 371 (c)(1),
(2), (4) Date: Aug. 29, 2011

(87) PCT Pub. No.: WO2010/068526
PCT Pub. Date: Jun. 17, 2010

(65) Prior Publication Data
US 2011/0306060 A1     Dec. 15, 2011

Related U.S. Application Data

(60) Provisional application No. 61/121,951, filed on Dec. 12, 2008.

(51) Int. Cl.
*G01N 33/573* (2006.01)
*G01N 33/543* (2006.01)
*C07K 16/40* (2006.01)

(52) U.S. Cl.
CPC ............. *C07K 16/40* (2013.01); *C07K 2317/55* (2013.01); *G01N 33/573* (2013.01); *G01N 33/543* (2013.01); *G01N 2333/96433* (2013.01)
USPC .......................................... 435/7.4; 435/7.94

(58) Field of Classification Search
None
See application file for complete search history.

(56) References Cited

U.S. PATENT DOCUMENTS

| | | |
|---|---|---|
| 2003/0119038 A1 | 6/2003 | Bingham et al. |
| 2004/0009553 A1 | 1/2004 | Glucksmann et al. |
| 2006/0040296 A1 | 2/2006 | Kozian et al. |
| 2008/0008697 A1 | 1/2008 | Mintier et al. |
| 2012/0208208 A1* | 8/2012 | Ni et al. ............. 435/7.4 |
| 2012/0219558 A1* | 8/2012 | Ni et al. ............. 424/146.1 |

FOREIGN PATENT DOCUMENTS

| | | |
|---|---|---|
| EP | 1 067 182 | 1/2001 |
| EP | 1 440 981 | 7/2004 |
| EP | 1 471 152 | 10/2004 |
| WO | WO 01/31007 | 5/2001 |
| WO | WO 01/34768 | 5/2001 |
| WO | WO 01/57081 | 8/2001 |
| WO | WO 01/77137 | 10/2001 |
| WO | WO 01/98468 | 12/2001 |
| WO | WO 02/14358 | 2/2002 |
| WO | WO 02/46383 | 6/2002 |
| WO | WO 02/090526 | 11/2002 |
| WO | WO 02/102993 | 12/2002 |
| WO | WO 02/102994 | 12/2002 |
| WO | WO 2008/057459 A2 * | 5/2008 |
| WO | WO 2008/125623 | 10/2008 |

OTHER PUBLICATIONS

Abifadel et al. (2003) *Nature Genetics* 34(2):154-156 "Mutations in PCSK9 cause autosomal dominant hypercholesterolemia".
Benjannet et al. (2004) *J Biol Chem.* 279(47):48865-75 "NARC-1/PCSK9 and its natural mutants: zymogen cleavage and effects on the low density lipoprotein (LDL) receptor and LDL cholesterol".
Cameron et al. {2006) *Hum Mol Genet.* 15(9):1551-8 "Effect of mutations in the PCSK9 gene on the cell surface LDL receptors".
Cohen et al. (2006) *N. Engl. J. Med.* 354(12):1264-1272 "Sequence variations in PCSK9, low LDL, and protection against coronary heart disease".
Dubuc et al. (2004) *Arterioscler Thromb Vasc Biol.* 24(8):1454-9 "Statins upregulate PCSK9, the gene encoding the proprotein convertase neural apoptosis-regulated convertase-1 implicated in familial hypercholesterolemia".
Genbank Accession No. NP_777596.2, PRI Aug. 31, 2012 (Sharotri et al.), (7 pages total).
Lagace et al. {2006) *J Clin Invest.* 116(11):2995-3005 "Secreted PCSK9 decreases the number LDL receptors in hepatocytes and in livers of parabiotic mice".
Law et al. (2003) *BMJ* 326(7404):1423-1427 "Quantifying effect of statins on low density lipoprotein cholesterol, ischaemic heart disease, and stroke: systematic review and meta-analysis".
Leren (2004) *Clin. Genet.* 65(5):419-422 "Mutations in the PCSK9 gene in Norwegian subjects with autosomal dominant hypercholesterolemia".
Maxwell et al. (2003) *J Lipid Res.* 44(11):2109-19 "Novel putative SREBP and LXR target genes identified by microarray analysis in liver of cholesterol-fed mice".

(Continued)

*Primary Examiner* — Christine Foster
(74) *Attorney, Agent, or Firm* — Sheela Mohan-Peterson

(57) ABSTRACT

Methods of using PCSK9 antagonists More specifically, methods for measuring circulating PCSK9 levels in a biological sample by means of an immunoassay The immunoassay used can be a solid phase immunoassay, such as a dissociation-enhanced lanthanide fluorescence immunoassay utilizing an E07 capture antibody or coating and a G08 or H23 detecting antibody.

3 Claims, 7 Drawing Sheets

(56) References Cited

OTHER PUBLICATIONS

Rashid et al. (2005) *Proc Natl Acad Sci U S A*. 102(15):5374-9 "Decreased plasma cholesterol and hypersensitivity to statins in mice lacking Pcsk9".

Seidah, et al. (2003) *Proc Natl Acad Sci U S A*. 100(3):928-33 "The secretory proprotein convertase neural apoptosis-regulated convertase 1 (NARC-1): liver regeneration and neuronal differentiation".

Timms et al. (2004) *Hum. Genet*. 114(4):349-353 "A mutation in PCSK9 causing autosomal-dominant hypercholesterolemia in a Utah pedigree".

\* cited by examiner

PCSK9 IMMUNOASSAY

BACKGROUND OF THE INVENTION

Proprotein convertase subtilisin-pexin type 9 (PCSK9), also known as neural apoptosis-regulated convertase 1 (NARC-1), is a proteinase K-like subtilase identified as the 9$^{th}$ member of the secretory subtilase family (Seidah, N. G., et al., 2003 PROC NATL ACAD SCI USA 100:928-933). PCSK9 is expressed in cells capable of proliferation and differentiation such as hepatocytes, kidney mesenchymal cells, intestinal ileum, colon epithelia and embryonic brain telencephalic neurons (Seidah et al., 2003).

The gene for human PCSK9 has been sequenced and found to be about 22-kb long with 12 exons that encode a 692 amino acid protein (NP_777596.2). PCSK9 is disclosed and/or claimed in several patent publications, including: PCT Publication Nos. WO 01/31007, WO 01/57081, WO 02/14358, WO 01/98468, WO 02/102993, WO 02/102994, WO 02/46383, WO 02/90526, WO 01/77137, and WO 01/34768; US Publication Nos. US 2004/0009553 and US 2003/0119038, and European Publication Nos. EP 1 440 981, EP 1 067 182, and EP 1 471 152.

PCSK9 has been implicated in cholesterol homeostasis, as it appears to have a specific role in cholesterol biosynthesis or uptake. In a study of cholesterol-fed rats, Maxwell et al. found that PCSK9 was downregulated in a similar manner to other genes involved in cholesterol biosynthesis, (Maxwell et al., 2003 J. LIPID RES. 44:2109-2119). The expression of PCSK9 was regulated by sterol regulatory element-binding proteins (SREBP), which is seen in other genes involved in cholesterol metabolism (Maxwell, et al., 2003).

Additionally, PCSK9 expression is upregulated by statins in a manner attributed to the cholesterol-lowering effects of the drugs (Dubuc et al., 2004 ARTERTOSCLER. THROMB. VASC. BIOL. 24:1454-1459). Adenoviral expression of PCSK9 has been shown to lead to a notable time-dependent increase in circulating low density lipoprotein (LDL) (Benjannet et al., 2004 J. BIOL. CHEM. 279:48865-48875) and mice with PCSK9 gene deletions have increased levels of hepatic LDL receptors (LDLR) and clear LDL from the plasma more rapidly (Rashid et al., 2005 PROC. NATL. ACAD. SCI. USA 102:5374-5379). Medium from HepG2 cells transiently transfected with PCSK9 reduce the amount of cell surface LDLRs and internalization of LDL when transferred to untransfected HepG2 cells (Cameron et al., 2006 HUMAN MOL. GENET. 15:1551-1558). It has been further demonstrated that purified PCSK9 added to the medium of HepG2 cells had the effect of reducing the number of cell-surface LDLRs in a dose- and time-dependent manner (Lagace et al., 2006 J. CLIN. INVEST. 116:2995-3005).

A number of mutations in the gene PCSK9 have also been conclusively associated with autosomal dominant hypercholesterolemia (ADH), an inherited metabolism disorder characterized by marked elevations of low density lipoprotein ("LDL") particles in the plasma which can lead to premature cardiovascular failure (e.g., Abifadel et al., 2003 NATURE GENETICS 34:154-156; Timms et al., 2004 HUM. GENET. 114:349-353; Leren, 2004 CLIN. GENET. 65:419-422).

It therefore appears that PCSK9 plays a role in the regulation of LDL production. Expression or upregulation of PCSK9 is associated with increased plasma levels of LDL cholesterol, and inhibition or the lack of expression of PCSK9 is associated with low LDL cholesterol plasma levels. Significantly, lower levels of LDL cholesterol associated with sequence variations in PCSK9 confer protection against coronary heart disease (Cohen, et al., 2006 N. ENGL. J. MED. 354:1264-1272).

Clinical trial data has demonstrated that reductions in LDL cholesterol levels are related to the rate of coronary events (Law et al., 2003 BMJ 326:1423-1427). Moderate lifelong reduction in plasma LDL cholesterol levels has been shown to be substantially correlated with a substantial reduction in the incidence of coronary events (Cohen et al., 2006), even in populations with a high prevalence of non-lipid-related cardiovascular risk factors. Accordingly, there is great benefit to be reaped from the managed control of LDL cholesterol levels.

Accordingly, it would be desirable to further investigate PCSK9 as a target for the treatment of cardiovascular disease. Antibodies useful as PCSK9 antagonists have been identified and have utility as therapeutic agents. In support of such investigations, it would be useful to have a method for measuring levels of circulating PCSK9 in a biological sample which has been exposed to a PCSK9 antagonist, such as an antibody.

It would be further desirable to be able to identify novel PCSK9 antagonists in order to assist in the quest for compounds and/or agents effective in the treatment of cardiovascular disease. Hence, a method for measuring levels of circulating PCSK9 in a biological sample for such purposes as, e.g., assessing the effectiveness of a putative PCSK9 antagonist is desirable.

Additionally, it would be of use to provide kits to assay levels of circulating PCSK9 in biological samples.

SUMMARY OF THE INVENTION

The present invention relates to a method of measuring circulating PCSK9 levels in a biological sample. Said method comprises the steps of performing an immunoassay on a biological sample obtained from a subject and comparing the level of PCSK9 in said sample against a standard having a known concentration of PCSK9.

The present invention further relates to a method for identifying novel PCSK9 antagonists, comprising the steps of performing an immunoassay on a biological sample which has been contacted with a putative PCSK9 antagonist and comparing the level of PCSK9 in said sample against a standard having a known concentration of PCSK9.

A further aspect of the present invention relates to a kit for measuring circulating PCSK9 levels in a biological sample, wherein said kit comprises:

a) a biological sample collection device;

b) a composition comprising an immunoassay, comprising a coating or capture antibody and a detection antibody;

and c) a means for detecting a reaction between PCSK antigen in the sample and antibodies in the immunoassay.

DETAILED DESCRIPTION OF THE INVENTION

Figure 1:
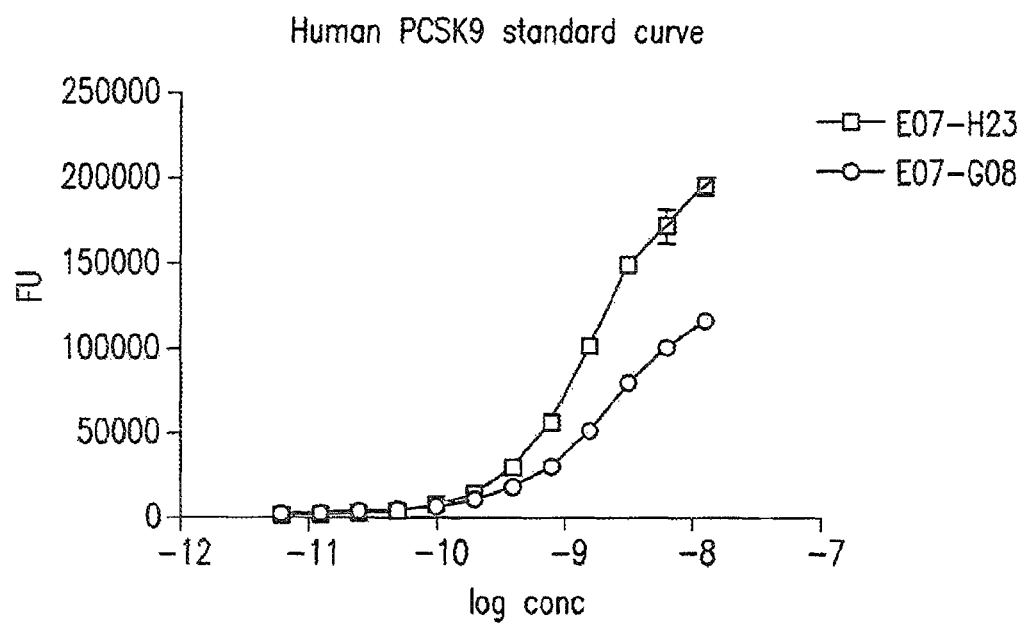
FIG. 1 illustrates a human PCSK9 DELFIA assay standard curve using the E07-G08 and E07-H23 formats.

The present invention relates to a method of measuring circulating PCSK9 levels in a biological sample, comprising the steps of performing an immunoassay on a biological sample obtained from a subject and comparing the level of PCSK9 in said sample against a standard having a known concentration of PCSK9.

In a preferred embodiment, the immunoassay is a solid phase immunoassay. In a more preferred embodiment, the solid phase immunoassay is a dissociation-enhanced lanthanide fluorescence immunoassay (DELFIA). However, it is within the scope of the current invention to use any solution-based or solid phase immunoassay as will be well familiar to those of skill in the art. Such assays include, without limitation, assays using magnetic beads as labels in lieu of enzymes, ELISAs, radioisotopes, or fluorescent moieties (fluorescent immunoassays).

The biological sample is selected from the group consisting of blood, plasma and serum.

The present invention further relates to a method for measuring PCSK9 in the presence of a putative PCSK9 antagonist. Said method comprises the steps of performing an immunoassay on a biological sample which has been contacted with a putative PCSK9 antagonist and comparing the level of PCSK9 in said sample against a standard having a known concentration of PCSK9. In a preferred embodiment, the immunoassay is a solid phase immunoassay. In a more preferred embodiment, the solid phase immunoassay is a dissociation-enhanced lanthanide fluorescence immunoassay (DELFIA).

The biological sample is selected from the group consisting of blood, plasma and serum.

The present invention additionally relates to a kit for measuring circulating PCSK9 levels in a biological sample, comprising:

a) a biological sample collection device;

b) a composition comprising an immunoassay, comprising a coating or capture antibody and a detection antibody;

and c) a means for detecting a reaction between PCSK antigen in the sample and antibodies in the immunoassay.

Kits typically but need not include a label indicating the intended use of the contents of the kit. The term label includes any writing, or recorded material supplied on or with the kit, or which otherwise accompanies the kit.

The following examples are provided to illustrate the present invention without limiting the same hereto:

Example 1

Characterization of the PCSK9 Antagonists

The PCSK9 antagonists used in this assay were antibodies E07, G08 and H23. G08 is disclosed in WO2008057459, which is incorporated in its entirety herein.

E07 and H23 are characterized as follows (complementarity-determining regions (CDRs) are designated in bold and underlined):

```
E07
Sequences of PCSK9_5_CX3_E07 Fab as expressed from Morphosys library in E. coli
Fab Vl3_3 light chain nucleotide sequence PCSK9_5_CX3_E07
                                                                    (SEQ ID NO: 1)
                                           CDR1
GATATCGAACTGACCCAGCCGCCTTCAGTGAGCGTTGCACCAGGTCAGACCGCGCGTATCTCGTGTAGCGGCGATTCTCTTCGTGATAAGTAT CDR2
GTTCATTGGTACCAGCAGAAACCCGGGCAGGCGCCAGTTGTTGTGATTTATTATGATACTAATCGTCCCTCAGGCATCCCGGAACGCTTTAGC CDR3
GGATCCAACAGCGGCAACACCGCGACCCTGACCATTAGCGGCACTCAGGCGGAAGACGAAGCGGATTATTATTGCGCTGCTTATACTCGTTCT ATTTATGTGTTTGGCGGCGGCACGAAGTTAACCGTTCTTGGCCAGCCGAAAGCCGCACCGAGTGTGACGCTGTTTCCGCCGAGCAGCGAAGAA TTGCAGGCGAACAAAGCGACCCTGGTGTGCCTGATTAGCGACTTTTATCCGGGAGCCGTGACAGTGGCCTGGAAGGCAGATAGCAGCCCCGTC AAGGCGGGAGTGGAGACCACCACACCCTCCAAACAAAGCAACAACAAGTACGCGGCCAGCAGCTATCTGAGCCTGACGCCTGAGCAGTGGAAG

TCCCACAGAAGCTACAGCTGCCAGGTCACGCATGAGGGGAGCACCGTGGAAAAAACCGTTGCGCCGACTGAGGCC

Fab VH3_3 heavy chain nucleotide sequence PCSK9_5_CX3_E07
                                                                    (SEQ ID NO: 2)
                                                           CDR1
CAGGTGCAATTGGTGGAAAGCGGCGGCGGCCTGGTGCAACCGGGCGGCAGCCTGCGTCTGAGCTGCGCGGCCTCCGGATTTACCTTTTCTGAT CDR2
CATTGGATGCATTGGGTGCGCCAAGCCCCTGGGAAGGGTCTCGAGTGGGTGAGCTATATCGATTATTATGGTAGCAATACCCATTATGCGGAT AGCGTGAAAGGCCGTTTTACCATTTCACGTGATAATTCGAAAAACACCCTGTATCTGCAAATGAACAGCCTGCGTGCGGAAGATACGGCCGTG CDR3
TATTATTGCGCGCGTATGCTTTATGGTTGGAATTATGGTGTTTTTGATTATTGGGGCCAAGGCACCCTGGTGACGGTTAGCTCAgcgtcgacc aaaggtccaagcgtgtttccgctggctc-
cgagcagcaaaagcaccagcggcggcacggctgccctgggctgcctggttaaagattatttcccgg aaccagtcaccgtgagctggaacagcggggcgctgaccagcggcgtgcataccttccggcggtgctgcaaagcagcggcctgtatagcctga
```

-continued gcagcgttgtgaccgtgccgagcagcagcttaggcactcagacctatatttgcaacgtgaaccataaaccgagcaacaccaaagtggataaaa aagtggaaccgaaaagcgaattcgagcagaagctgatctctgaggaggatctgaacggcgcgccgcaccatcatcaccatcac Fab Vl3_3 light chain amino acid sequence PCSK9_5_CX3_E07

(SEQ ID NO: 3)

CDR1  CDR2  CDR3
DIELTQPPSVSVAPGQTARISCSGDSLRDKYVHWYQQKPGQAPVVVIYYDTNRPSGIPERFSGSNSGNTATLTISGTQAEDEADYYCAAYTRS

IYVFGGGTKLTVLGQPKAAPSVTLFPPSSEELQANKATLVCLISDFYPGAVTVAWKADSSPVKAGVETTTPSKQSNNKYAASSYLSLTPEQWK

SHRSYSCQVTHEGSTVEKTVAPTEA

Fab VH3_3 heavy chain amino acid sequence PCSK9_5_CX3_E07

(SEQ ID NO: 4)

CDR1  CDR2
QVQLVESGGGLVQPGGSLRLSCAASGFTFSDHWMHWVRQAPGKGLEWVSYIDYYGSNTHYADSVKGRFTISRDNSKNTLYLQMNSLRAEDTAV

CDR3
YYCARMLYGWNYGVFDYWGQGTLVTVSSASTKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSEFEQKLISEEDLNGAPHHHHHH

Sequences of PCSK9_5_CX3_E07 IgG2M4 as expressed in Mammalian cell culture
IgG Vl3_3 light chain nucleotide sequence PCSK9_5_CX3_E07

(SEQ ID NO: 5)

CDR1
GATATCGAACTGACCCAGCCGCCTTCAGTGAGCGTTGCACCAGGTCAGACCGCGCGTATCTCGTGTAGCGGCGATTCTCTTCGTGATAAGTAT

CDR2
GTTCATTGGTACCAGCAGAAACCCGGGCAGGCGCCAGTTGTTGTGATTTATTATGATACTAATCGTCCCTCAGGCATCCCGGAACGCTTTAGC

CDR3
GGATCCAACAGCGGCAACACCGCGACCCTGACCATTAGCGGCACTCAGGCGGAAGACGAAGCGGATTATTATTGCGCTGCTTATACTCGTTCT

ATTTATGTGTTTGGCGGCGGCACGAAGTTAACCGTTCTTGGCCAGCCCAAGGCCAACCCCACCGTGACCCTGTTCCCCCCATCTTCTGAGGAG

CTGCAAGCCAACAAGGCCACCCTGGTGTGCCTGATCTCTGACTTCTACCCTGGCGCTGTGACAGTGGCCTGGAAGGCTGATGGCTCTCCTGTG

AAGGCTGGCGTGGAGACCACCAAGCCATCTAAGCAGTCTAACAACAAGTATGCTGCCTCTTCTTACCTGTCTCTGACCCCTGAGCAGTGGAAG

AGCCACCGGTCTTACTCTTGCCAGGTGACCCATGAGGGCTCTACAGTGGAGAAGACAGTGGCCCCCACAGAGTGCTCT

IgG2M4 VH3_3 heavy chain nucleotide sequence PCSK9_5_CX3_E07

(SEQ ID NO: 6)

CDR1
CAGGTGCAATTGGTGGAAAGCGGCGGCGGCCTGGTGCAACCGGGCGGCAGCCTGCGTCTGAGCTGCGCGGCCTCCGGATTTACCTTTTCTGAT

CDR2
CATTGGATGCATTGGGTGCGCCAAGCCCCTGGGAAGGGTCTCGAGTGGGTGAGCTATATCGATTATTATGGTAGCAATACCCATTATGCGGAT

AGCGTGAAAGGCCGTTTTACCATTTCACGTGATAATTCGAAAAACACCCTGTATCTGCAAATGAACAGCCTGCGTGCGGAAGATACGGCCGTG

CDR3
TATTATTGCGCGCGTATGCTTTATGGTTGGAATTATGGTGTTTTTGATTATTGGGGCCAAGGCACCCTGGTGACGGTTAGCTCAGCATCCACC

AAGGGCCCATCCGTCTTCCCCCTGGCGCCCTGCTCCAGGAGCACCTCCGAGAGCACAGCCGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCCTCAGGACTCTACTCCCTC

AGCAGCGTGGTGACCGTGACCTCCAGCAACTTTGGCACGCAGACCTACACCTGCAACGTAGATCACAAGCCCAGCAACACCAAGGTGGACAAG

ACAGTTGAGCGGAAATGCTGCGTGGAGTGCCCACCATGCCCAGCACCTCCAGTGGCCGGACCATCAGTCTTCCTGTTCCCCCCAAAACCCAAG

GACACTCTCATGATCTCCCGGACCCCTGAGGTCACGTGCGTGGTGGTGGACGTGAGCCAGGAAGACCCCGAGGTCCAGTTCAACTGGTACGTG

GATGGCGTGGAGGTGCATAATGCCAAGACAAAGCCGCGGGAGGAGCAGTTCAACAGCACGTTCCGTGTGGTCAGCGTCCTCACCGTCCTGCAC

CAGGACTGGCTGAACGGCAAGGAGTACAAGTGCAAGGTCTCCAACAAAGGCCTCCCGTCCTCCATCGAGAAAACCATCTCCAAAACCAAAGGG

CAGCCCCGAGAGCCACAGGTGTACACCCTGCCCCCATCCCGGGAGGAGATGACCAAGAACCAGGTCAGCCTGACCTGCCTGGTCAAAGGCTTC

TACCCCAGCGACATCGCCGTGGAGTGGGAGAGCAATGGGCAGCCGGAGAACAACTACAAGACCACGCCTCCCATGCTGGACTCCGACGGCTCC

TTCTTCCTCTACAGCAAGCTAACCGTGGACAAGAGCAGGTGGCAGCAGGGGAATGTCTTCTCATGCTCCGTGATGCATGAGGCTCTGCACAAC

CACTACACACAGAAGAGCCTCTCCCTGTCTCCTGGTAAA

IgG Vl3_3 light chain amino acid sequence PCSK9_5_CX3_E07

(SEQ ID NO: 7)

CDR1                           CDR2                                   CDR3
DIELTQPPSVSVAPGQTARISCSGDSLRDKYVHWYQQKPGQAPVVIYYDTNRPSGIPERFSGSNSGNTATLTISGTQAEDEADYYCAAYTRS

IYVFGGGTKLTVLGQPKANPTVTLFPPSSEELQANKATLVCLISDFYPGAVTVAWKADGSPVKAGVETTKPSKQSNNKYAASSYLSLTPEQWK

SHRSYSCQVTHEGSTVEKTVAPTECS

IgG2m4 VH3_3 heavy chain amino acid sequence PCSK9_5_CX3_E07

(SEQ ID NO: 8)

CDR1                           CDR2
QVQLVESGGGLVQPGGSLRLSCAASGFTFSDHWMHWVRQAPGKGLEWVSYIDYYGSNTHYADSVKGRFTISRDNSKNTLYLQMNSLRAEDTAV

CDR3
YYCARMLYGWNYGVFDYWGQGTLVTVSSASTKGPSVFPLAPCSRSTSESTAALGCLVKDYFPEPVTVSWNSGALTSGVHTFPAVLQSSGLYSL

SSVVTVTSSNFGTQTYTCNVDHKPSNTKVDKTVERKCCVECPPCPAPPVAGPSVFLFPPKPKDTLMISRTPEVTCVVVDVSQEDPEVQFNWYV

DGVEVHNAKTKPREEQFNSTFRVVSVLTVLHQDWLNGKEYKCKVSNKGLPSSIEKTISKTKGQPREPQVYTLPPSREEMTKNQVSLTCLVKGF

YPSDIAVEWESNGQPENNYKTTPPMLDSDGSFFLYSKLTVDKSRWQQGNVFSCSVMHEALHNHYTQKSLSLSPGK

H23
Sequences of PCSK9_6_CX1_H23 Fab as expressed from Morphosys library in *E. coli*
Fab Vk3_3b light chain nucleotide sequence PCSK9_6_CX1_H23

(SEQ ID NO: 9)

CDR1
GATATCGTGCTGACCCAGAGCCCGGCGACCCTGAGCCTGTCTCCGGGCGAACGTGCGACCCTGAGCTGCAGAGCGAGCCAGTCTGTTAATTCT

CDR2
AATTATCTGGCTTGGTACCAGCAGAAACCAGGTCAAGCACCGCGTCTATTAATTTATGGTGCTTCTTCTCGTGCAACTGGGGTCCCGGCGCGT

CDR3
TTTAGCGGCTCTGGATCCGGCACGGATTTTACCCTGACCATTAGCAGCCTGGAACCTGAAGACTTTGCGGTTTATTATTGCCAGCAGTGGGGT

GATGTTCCTATTACCTTTGGCCAGGGTACGAAAGTTGAAATTAAACGTACGgtggctgctccgagcgtgttttattttccgccgagcgatgaa caactgaaaagcggcacggcgagcgtggtgtgcctgctgaacaacttttatccgcgtgaagcgaaagttcagtggaaagtagacaacgcgctg caaagcggcaacagccaggaaagcgtgaccgaacaggatagcaaagatagccacctattctctgagcagcaccctgaccctgagcaaagcggat tatgaaaaacataaagtgtatgcgtgcgaagtgacccatcaaggtctgagcagcccggtgactaaatcttttaatcgtggcgaggcc Fab VH3_3 heavy chain nucleotide sequence PCSK9_6_CX1_H23

(SEQ ID NO: 10)

CDR1
CAGGTGCAATTGGTGGAAAGCGGCGGCGGCCTGGTGCAACCGGGCGGCAGCCTGCGTCTGAGCTGCGCGGCCTCCGGATTTACCTTTTCTGAT

CDR2
TATTATATGCATTGGGTGCGCCAAGCCCCTGGGAAGGGTCTCGAGTGGGTGAGCAATATCTCTGGTTCTGGTAGCACTACCTATTATGCGGAT

AGCGTGAAAGGCCGTTTTACCATTTCACGTGATAATTCGAAAAACACCCTGTATCTGCAAATGAACAGCCTGCGTGCGGAAGATACGGCCGTG

CDR3
TATTATTGCGCGCGTGGTATGTTTGATTTTTGGGGCCAAGGCACCCTGGTGACGGTTAGCTCAgcgtcgaccaaaggtccaagcgtgtttccg ctggctccgagcagcaaaagcaccagcggcggcacggctgccctgggctgcctggttaaagattatttcccggaaccagtcaccgtgagctgg aacagcggggcgctgaccagcggcgtgcataccttccggcggtgctgcaaagcagcggcctgtatagcctgagcagcgttgtgaccgtgccg agcagcagcttaggcactcagacctatatttgcaacgtgaaccataaaccgagcaacaccaaagtggataaaaaagtggaaccgaaaagcgaa ttcgagcagaagctgatctctgaggaggatctgaacggcgcgccgcaccatcatcaccatcac Fab Vk3_3b light chain amino acid sequence PCSK9_6_CX1_H23

(SEQ ID NO: 11)

CDR1                            CDR2                                            CDR3
DIVLTQSPATLSLSPGERATLSCRASQSVNSNYLAWYQQKPGQAPRLLIYGASSRATGVPARFSGSGSGTDFTLTISSLEPEDFAVYYCQQWG

DVPITFGQGTKVEIKRTVAAPSVFIFPPSDEQLKSGTASVVCLLNNFYPREAKVQWKVDNALQSGNSQESVTEQDSKDSTYSLSSTLTLSKAD

YEKHKVYACEVTHQGLSSPVTKSFNRGEA

Fab VH3_3 amino acid sequence PCSK9_6_CX1_H23

(SEQ ID NO: 12)

CDR1                           CDR2
QVQLVESGGGLVQPGGSLRLSCAASGFTFSDYYMHWVRQAPGKGLEWVSNISGSGSTYYADSVKGRFTISRDNSKNTLYLQMNSLRAEDTAVY

CDR3

YCARGMFDFWGQGTLVTVSSASTKGPSVFPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSEFEQKLISEEDLNGAPHHHHHH

Sequences of PCSK9_6_CX1_H23 IgG2M4 as expressed in Mammalian cell culture
IgG Vk3_3b light chain nucleotide sequence PCSK9_6_CX1_H23

(SEQ ID NO: 13)

CDR1
GATATCGTGCTGACCCAGAGCCCGGCGACCCTGAGCCTGTCTCCGGGCGAACGTGCGACCCTGAGCTGCAGAGCGAGCCAGTCTGTTAATTCT

CDR2
AATTATCTGGCTTGGTACCAGCAGAAACCAGGTCAAGCACCGCGTCTATTAATTTATGGTGCTTCTTCTCGTGCAACTGGGGTCCCGGCGCGT

CDR3
TTTAGCGGCTCTGGATCCGGCACGGATTTTACCCTGACCATTAGCAGCCTGGAACCTGAAGACTTTGCGGTTTATTATTGCCAGCAGTGGGGT

GATGTTCCTATTACCTTTGGCCAGGGTACGAAAGTTGAAATTAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAGCACCTACAGCCTCAGCAGCACCCTGACGCTGAGCAAAGCAGAC

TACGAGAAACACAAAGTCTACGCCTGCGAAGTCACCCATCAGGGCCTGAGCTCGCCCGTCACAAAGAGCTTCAACAGGGGAGAGTGT

IgG2M4 VH3_3 heavy chain nucleotide sequence PCSK9_6_CX1_H23

(SEQ ID NO: 14)

CDR1
CAGGTGCAATTGGTGGAAAGCGGCGGCGGCCTGGTGCAACCGGGCGGCAGCCTGCGTCTGAGCTGCGCGGCCTCCGGATTTACCTTTTCTGAT

CDR2
TATTATATGCATTGGGTGCGCCAAGCCCCTGGGAAGGGTCTCGAGTGGGTGAGCAATATCTCTGGTTCTGGTAGCACTACCTATTATGCGGAT

AGCGTGAAAGGCCGTTTTACCATTTCACGTGATAATTCGAAAAACACCCTGTATCTGCAAATGAACAGCCTGCGTGCGGAAGATACGGCCGTG

CDR3
TATTATTGCGCGCGTGGTATGTTTGATTTTTGGGGCCAAGGCACCCTGGTGACGGTTAGCTCAGCATCCACCAAGGGCCCATCCGTCTTCCCC

CTGGCGCCCTGCTCCAGGAGCACCTCCGAGAGCACAGCCGCCCTGGGCTGCCTGGTCAAGGACTACTTCCCCGAACCGGTGACGGTGTCGTGG

AACTCAGGCGCCCTGACCAGCGGCGTGCACACCTTCCCGGCTGTCCTACAGTCCTCAGGACTCTACTCCCTCAGCAGCGTGGTGACCGTGACC

TCCAGCAACTTTGGCACGCAGACCTACACCTGCAACGTAGATCACAAGCCCAGCAACACCAAGGTGGACAAGACAGTTGAGCGGAAATGCTGC

GTGGAGTGCCCACCATGCCCAGCACCTCCAGTGGCCGGACCATCAGTCTTCCTGTTCCCCCCAAAACCCAAGGACACTCTCATGATCTCCCGG

ACCCCTGAGGTCACGTGCGTGGTGGTGGACGTGAGCCAGGAAGACCCCGAGGTCCAGTTCAACTGGTACGTGGATGGCGTGGAGGTGCATAAT

GCCAAGACAAAGCCGCGGGAGGAGCAGTTCAACAGCACGTTCCGTGTGGTCAGCGTCCTCACCGTCCTGCACCAGGACTGGCTGAACGGCAAG

GAGTACAAGTGCAAGGTCTCCAACAAAGGCCTCCCGTCCTCCATCGAGAAAACCATCTCCAAAACCAAAGGGCAGCCCCGAGAGCCACAGGTG

TACACCCTGCCCCCATCCCGGGAGGAGATGACCAAGAACCAGGTCAGCCTGACCTGCCTGGTCAAAGGCTTCTACCCCAGCGACATCGCCGTG

GAGTGGGAGAGCAATGGGCAGCCGGAGAACAACTACAAGACCACGCCTCCCATGCTGGACTCCGACGGCTCCTTCTTCCTCTACAGCAAGCTA

ACCGTGGACAAGAGCAGGTGGCAGCAGGGGAATGTCTTCTCATGCTCCGTGATGCATGAGGCTCTGCACAACCACTACACACAGAAGAGCCTC

TCCCTGTCTCCTGGTAAA

IgG Vk3_3b light chain amino acid sequence PCSK9_6_CX1_H23

(SEQ ID NO: 15)

CDR1             CDR2                      CDR3
DIVLTQSPATLSLSPGERATLSCRASQSVNSNYLAWYQQKPGQAPRLLIYGASSRATGVPARFSGSGSGTDFTLTISSLEPEDFAVYYCQQWG

DVPITFGQGTKVEIKRTVAAPSVFIFPPSDEQLKSGTASVVCLLNNFYPREAKVQWKVDNALQSGNSQESVTEQDSKDSTYSLSSTLTLSKAD

YEKHKVYACEVTHQGLSSPVTKSFNRGEC

IgG2m4 VH3_3 heavy chain amino acid sequence PCSK9_6_CX1_H23

(SEQ ID NO: 16)

CDR1          CDR2
QVQLVESGGGLVQPGGSLRLSCAASGFTFSDYYMHWVRQAPGKGLEWVSNISGSGSTTYYADSVKGRFTISRDNSKNTLYLQMNSLRAEDTAV

CDR3
YYCARGMFDFWGQGTLVTVSSASTKGPSVFPLAPCSRSTSESTAALGCLVKDYFPEPVTVSWNSGALTSGVHTFPAVLQSSGLYSLSSVVTVT

SSNFGTQTYTCNVDHKPSNTKVDKTVERKCCVECPPCPAPPVAGPSVFLFPPKPKDTLMISRTPEVTCVVVDVSQEDPEVQFNWYVDGVEVHN

AKTKPREEQFNSTFRVVSVLTVLHQDWLNGKEYKCKVSNKGLPSSIEKTISKTKGQPREPQVYTLPPSREEMTKNQVSLTCLVKGFYPSDIAV

EWESNGQPENNYKTTPPMLDSDGSFFLYSKLTVDKSRWQQGNVFSCSVMHEALHNHYTQKSLSLSPGK

Example 2

Solid Phase Immunoassay (DELFIA)

96-well plates (high-binding 4HBX plates from Thermo-Labsystems, part #3855) were coated overnight at 4° with 50 µl of 10 µg/ml of anti-PCSK9 antibody (E07), the coating/capture antibody. The next day, the wells were blocked with 250 µl of blocking solution (1% BSA in TBS with 0.05% Tween-20) for 1 hour at room temperature. Plates were washed in a plate-washer with wash buffer (imidazole buffered saline with Tween 20 (KPL)). For the standard, purified human PCSK9 protein was titrated starting at 1 µg/ml. Purified human PCSK9 protein was diluted in assay buffer (1% BSA in PBS) and 100 µl of dilute protein was added on the plate as standard. Plates were incubated at 37° for 1 hour. Plates were again washed in a plate-washer with wash buffer.

Subsequently, the detection step was carried out. 1 µg/ml of biotinylated G08 or H23 was used as detecting antibody. 100 µl of 1 µg/ml biotinylated anti-PCSK9 IgG (H23 or G08) was added on the plates. After the plates were washed, 75 µl of 1:1000 Streptavidin/Europium (Perkin Elmer, part #1244-360) (diluted in assay buffer) was added. The plates were then incubated at room temperature for 20 minutes. The plates were washed again followed by the addition of 100 µl of DELFIA Enhance solution (Perkin Elmer part #1244-105) in order to enhance the fluorescence. The europium fluorescence was measured using a plate reader after one hour.

As mentioned in Example 1, all the anti-PCSK9 antibodies used are specific for human PCSK9 and were generated at Merck. The sensitivity of this assay, with either E07-G08 or E07-H23 paired format, is ~100 pM with a signal to noise ratio of >2.

Figure 2:
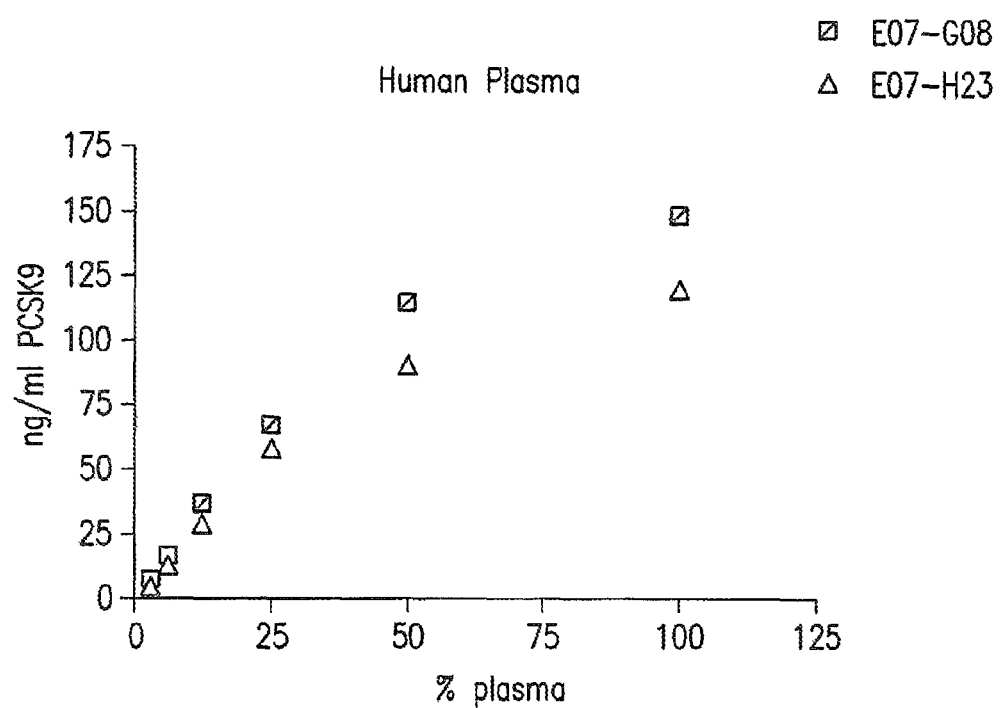
FIG. 2 shows the DELFIA assay tolerance for human serum/plasma.

As shown in FIG. 1, PCSK9 levels rang from 100-400 ng/ml in these samples and there is excellent agreement between the two DELFIA formats. Over 90 additional antibody pairs have been tested and none were as sensitive as these two antibody pairs (data not shown), FIG. 2 illustrates the DELFIA human plasma assay tolerance. Here, PCSK9 levels from healthy individuals were tested in human PCSK9 DELFIA using E07-H23 and E07-G08 format. Human plasma samples were diluted 4 fold before testing. Results are mean±SD, n=3. Human plasma sample was diluted with assay buffer (1% BSA in PBS) and then assayed in PCSK9 ELISA using either E07-G08 or E07-H23 format. As shown in FIG. 2, this assay can tolerate up to 25% of human plasma.

Figure 3:
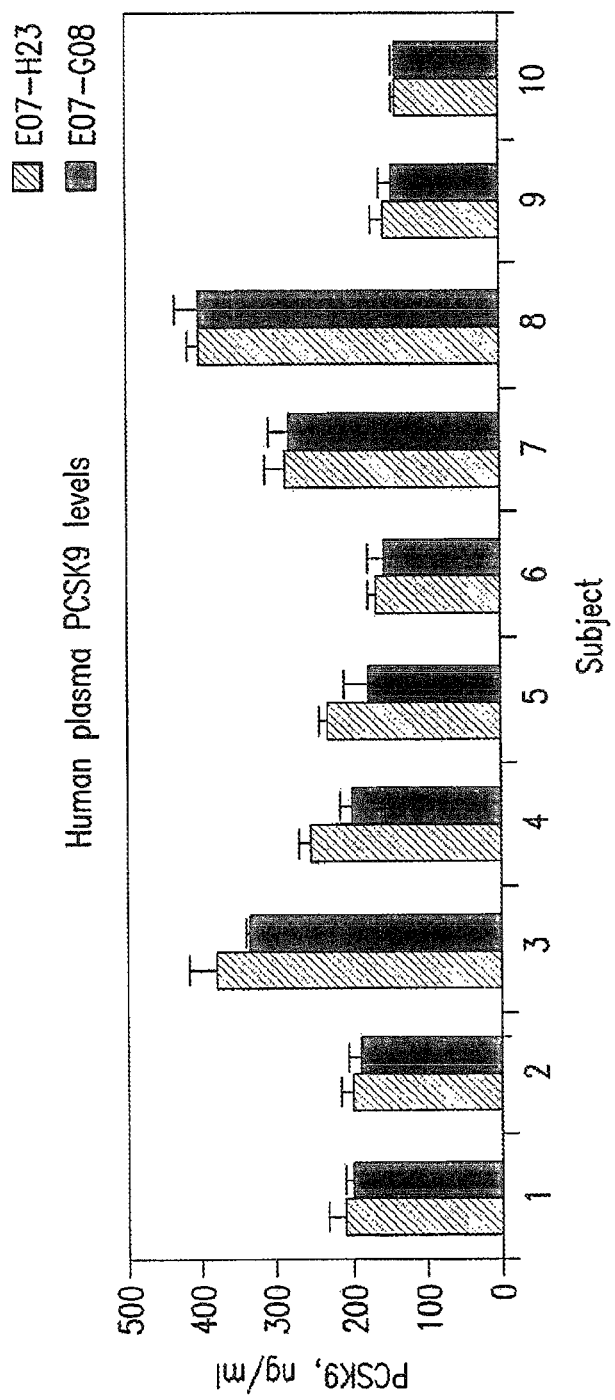
FIG. 3 gives a comparison of human plasma PCSK9 levels measured by PCSK9 DELFIA assays using both antibody pairs.

As shown in FIG. 3, PCSK9 levels were assessed in ten human subjects and range from 100-400 ng/ml in these samples. Again, there is excellent agreement between the two DELFIA formats.

Figure 4:
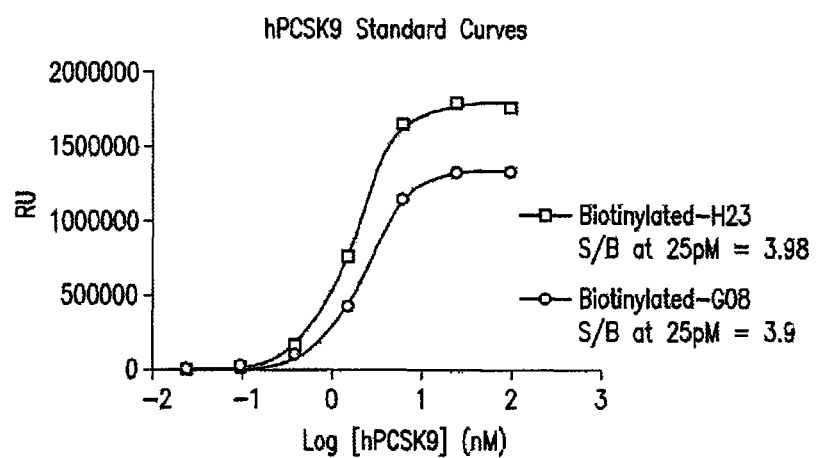
FIG. 4 illustrates a human PCSK9 MESO assay standard curve using the E07-G08 format.

In the study depicted in FIG. 4, 400 nM of anti-PCSK9 antibody, E07, was used as coating or capture antibody. Purified human PCSK9 protein was titrated starting at 100 nM. 2 ug/ml of biotinylated G08 or H23 IgG was used as detection antibody. As shown in FIG. 4, sensitivity of this assay is greater than 25 pM.

Example 3

Solid Phase Immunoassay

This assay was carried out using an electrochemical-based immunoassay system sold by Meso Scale Discovery (MSD, Gaithersburg, Md., USA, affiliated with IGEN International, Inc.). The wells of a 96 well standard Meso Scale Discovery plate were coated overnight at 4° C. with 504 of E07 antibody solution, at a concentration of 10 µg/mL. The following day, the wells were washed three times with wash buffer, and blocked for 1 hour at room temperature with 150 µL 3% BSA in wash buffer, with shaking. Next, 50 µL of recombinant human PCSK9 standards (varying concentrations of diluted recombinant protein) were added to the wells as a standard curve. Plasma samples were then diluted 1:4 in sample diluent and added to their respective wells. The plate was allowed to incubate for 1 hour at 37° C., 100% humidity, with shaking. Following incubation, the wells were washed three times with wash buffer; and 25 µL of a 2 µg/mL 5 equimolar biotinylated-G08 or H23 antibody was added for a 60 minute incubation at room temperature, with shaking.

After decanting, wells were washed three times with wash buffer to remove the unbound G08 antibody, and 25 µL of a 2 µg/mL Streptavidin-RU solution was added to the wells for hour incubation at room temperature, with shaking. Subsequently, after decanting, the wells were washed three times with wash buffer and 150 µL of 1× Read buffer T (without surfactant) was then added to all wells. The plate was read immediately on the Sector imager and Prism, version 4, was used to fit the standard curves.

Figure 5:
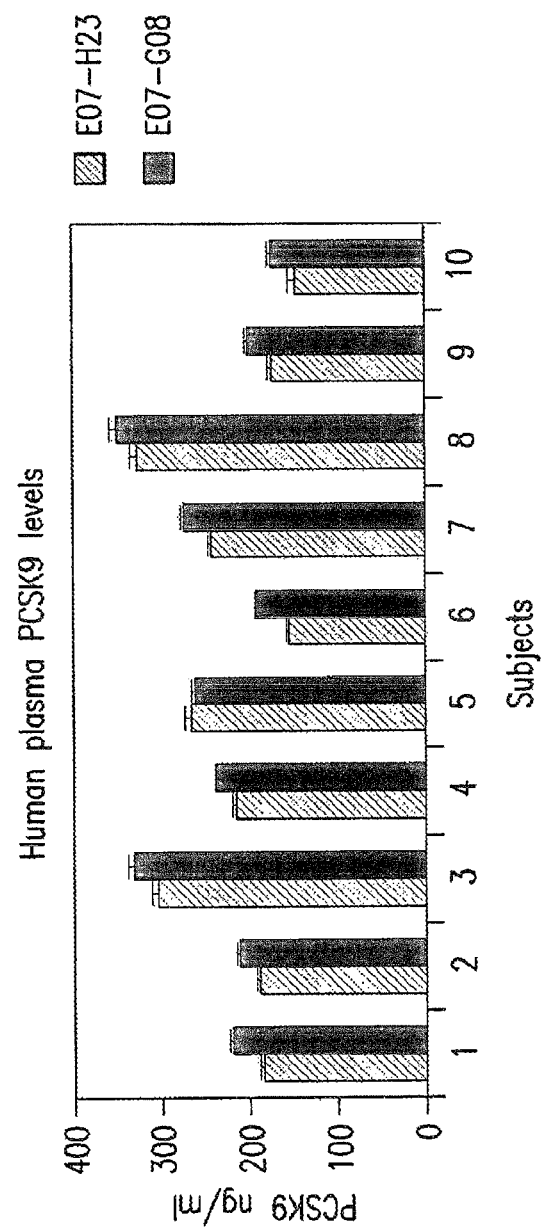
FIG. 5 depicts human serum or plasma PCSK9 levels measured by PCSK9 mesoscale assays.

PCSK9 levels from healthy individuals were tested in human PCSK9 mesoscale assay using E07-G08 format and E07-H23 format. Plasma samples were diluted 4 fold before testing. Results are mean±SD, n=3. As shown in FIG. 5, PCSK9 levels rang from 100-400 ng/ml in these samples. There is excellent agreement between the two mesoscale formats, as well as between the DELFIA (FIG. 4) and mesoscale methods.

Example 4

Figure 6:
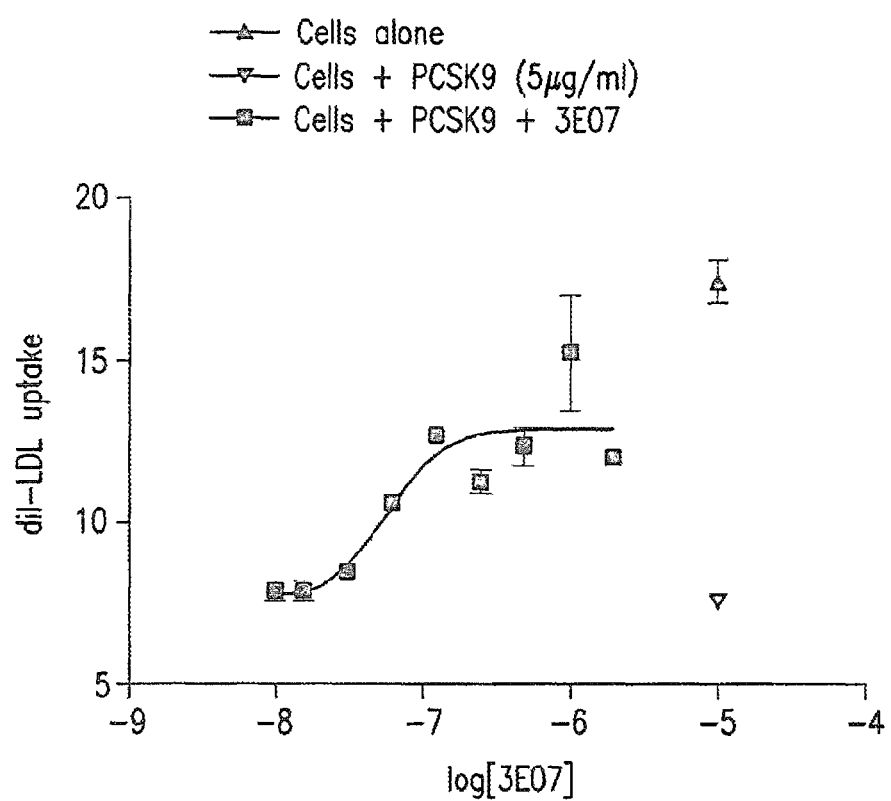
FIG. 6 shows that the E07 Fab is a partial inhibitor of PCSK9 function.

Functional Analysis of E07, G08 and H23 Fab 30,000 HEK293 cells/well were seeded in normal serum conditions and 24 hours later, media was changed to one lacking serum. 24 hours after that, LDL uptake was measured. 3E07 Fab was titrated with 5 ug/ml of hPCSK9 purified protein, starting at 100 ug/ml. The data in FIG. 6 demonstrate that E07 Fab is a partial inhibitor of PCSK9 function. The E07 Fab displays about 50% inhibition on the effect of hPCSK9.

Example 5

E07, H23 and G08 do not Compete with Binding of a Known PCSK9 Antagonist ("1B20")

Figure 7:
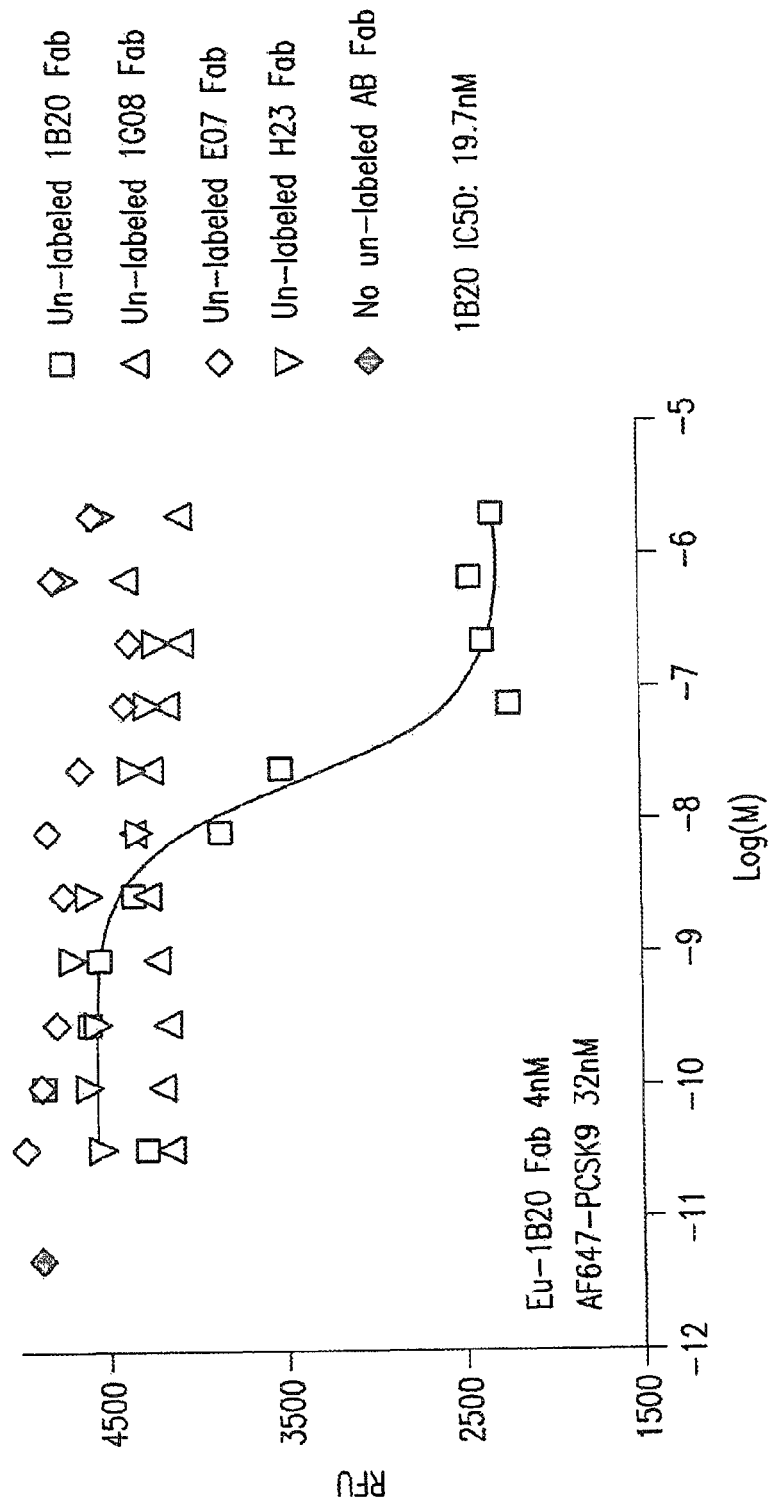
FIG. 7 shows that E07, G08 and H23 (Fab) do not compete with 1B20 IgG for PCSK9 binding.

As seen in FIG. 7, E07, G08 and H23 (Fab) do not compete with 1B20 IgG for PCSK9 binding. For this experiment, 4 nM (final concentration) of Eu-1G08 Fab was mixed with 32 nM (final concentration) of AF647-PCSK9 and various concentrations (from 1 µM to 50 pM) of unlabeled 1B20, G08, E07 and H23 Fab in 50 µl of assay buffer (10 mM HEPES pH 7.4, 150 mM NaCl, 0.05% BSA, 100 µM $CaCl_2$) in a black U-Bottom shaped pigmented styrene 96-well microtiter plate (Dynatech). The mixtures were Incubated at room temperature for 3 hours and plate was read on a Ruby Star fluorescent reader (available from BMG Technologies, Inc.) at Ex 370 mm. Signals were recorded at both 620 mm and 665 mm. The 665 mm/620 mm ratio was used to calculate the results. The experiments were performed in triplicate and repeated 3 times. The background of the assay is ~2340 RFU.

What is claimed is:

1. A method of measuring circulating Proprotein Convertase Subtilisin-Kexin 9 (PCSK9) levels in a biological sample obtained from a subject, comprising the steps of performing a solid phase immunoassay on the biological sample to determine a level of PCSK9 therein and comparing the level of PCSK9 in the biological sample against a standard having a known concentration of PCSK9, wherein the immunoassay is performed using a coating or capture antibody that is E07 and a detecting antibody that is H23; and wherein:

a) the E07 antibody comprises a light chain consisting of the amino acid sequence of SEQ ID NO: 3 or 7, and a heavy chain consisting of the amino acid sequence of SEQ ID NO: 4 or 8; and
b) the H23 antibody comprises a light chain consisting of the amino acid sequence of SEQ ID NO: 11 or 15, and a heavy chain consisting of the amino acid sequence of SEQ ID NO: 12 or 16.

2. The method of claim 1, wherein the solid phase immunoassay is a dissociation-enhanced lanthanide fluorescence immunoassay (DELFIA).

3. The method of claim 1, wherein the sample is selected from the group consisting of blood, plasma and serum.

* * * * *

SEQUENCE LISTING

<160> NUMBER OF SEQ ID NOS: 16

<210> SEQ ID NO 1
<211> LENGTH: 633
<212> TYPE: DNA
<213> ORGANISM: Homo Sapien

<400> SEQUENCE: 1

```
gatatcgaac tgacccagcc gccttcagtg agcgttgcac caggtcagac cgcgcgtatc      60
tcgtgtagcg gcgattctct tcgtgataag tatgttcatt ggtaccagca gaaacccggg     120
caggcgccag ttgttgtgat ttattatgat actaatcgtc cctcaggcat cccggaacgc     180
tttagcggat ccaacagcgg caacaccgcg accctgacca ttagcggcac tcaggcggaa     240
gacgaagcgg attattattg cgctgcttat actcgttcta tttatgtgtt tggcggcggc     300
acgaagttaa ccgttcttgg ccagccgaaa gccgcaccga gtgtgacgct gtttccgccg     360
agcagcgaag aattgcaggc gaacaaagcg accctggtgt gcctgattag cgacttttat     420
ccgggagccg tgacagtggc ctggaaggca gatagcagcc cgtcaaggc gggagtggag      480
accaccacac cctccaaaca agcaacaac aagtacgcgg ccagcagcta tctgagcctg      540
acgcctgagc agtggaagtc ccacagaagc tacagctgcc aggtcacgca tgaggggagc     600
accgtggaaa aaaccgttgc gccgactgag gcc                                  633
```

<210> SEQ ID NO 2
<211> LENGTH: 735
<212> TYPE: DNA
<213> ORGANISM: Homo Sapien

<400> SEQUENCE: 2

```
caggtgcaat tggtggaaag cggcggcggc ctggtgcaac cgggcggcag cctgcgtctg      60
agctgcgcgg cctccggatt taccttttct gatcattgga tgcattgggt gcgccaagcc     120
cctgggaagg gtctcgagtg ggtgagctat atcgattatt atggtagcaa tacccattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtatgctt     300
tatggttgga attatggtgt ttttgattat tggggccaag gcaccctggt gacggttagc     360
tcagcgtcga ccaaaggtcc aagcgtgttt ccgctggctc cgagcagcaa aagcaccagc     420
ggcggcacgg ctgccctggg ctgcctggtt aaagattatt cccggaacc agtcaccgtg      480
agctggaaca gcggggcgct gaccagcggc gtgcatacct ttccggcggt gctgcaaagc     540
agcggcctgt atagcctgag cagcgttgtg accgtgccga gcagcagctt aggcactcag     600
acctatattt gcaacgtgaa ccataaaccg agcaacacca agtggataa aaaagtggaa      660
ccgaaaagcg aattcgagca gaagctgatc tctgaggagg atctgaacgg cgcgccgcac     720
catcatcacc atcac                                                     735
```

<210> SEQ ID NO 3
<211> LENGTH: 211
<212> TYPE: PRT
<213> ORGANISM: Homo Sapien

<400> SEQUENCE: 3

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Arg Asp Lys Tyr Val

```
                     20                  25                  30
His Trp Tyr Gln Gln Lys Pro Gly Gln Ala Pro Val Val Ile Tyr
             35                  40                  45

Tyr Asp Thr Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ala Tyr Thr Arg Ser Ile Tyr Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
                115                 120                 125

Lys Ala Thr Leu Val Cys Leu Ile Ser Asp Phe Tyr Pro Gly Ala Val
                130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
                195                 200                 205

Thr Glu Ala
    210

<210> SEQ ID NO 4
<211> LENGTH: 245
<212> TYPE: PRT
<213> ORGANISM: Homo Sapien

<400> SEQUENCE: 4

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp His
                 20                  25                  30

Trp Met His Trp Val Arg Gln Ala Pro Gly Lys Gly Leu Glu Trp Val
             35                  40                  45

Ser Tyr Ile Asp Tyr Tyr Gly Ser Asn Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Leu Tyr Gly Trp Asn Tyr Gly Val Phe Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
                    180                 185                 190
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe Glu Gln Lys Leu Ile Ser Glu Glu Asp Leu Asn Gly Ala Pro His
225                 230                 235                 240

His His His His His
            245

<210> SEQ ID NO 5
<211> LENGTH: 636
<212> TYPE: DNA
<213> ORGANISM: Homo Sapien

<400> SEQUENCE: 5
gatatcgaac tgacccagcc gccttcagtg agcgttgcac caggtcagac cgcgcgtatc      60
tcgtgtagcg gcgattctct tcgtgataag tatgttcatt ggtaccagca gaaacccggg     120
caggcgccag ttgttgtgat ttattatgat actaatcgtc cctcaggcat cccggaacgc     180
tttagcggat ccaacagcgg caacaccgcg accctgacca ttagcggcac tcaggcggaa     240
gacgaagcgg attattattg cgctgcttat actcgttcta tttatgtgtt tggcggcggc     300
acgaagttaa ccgttcttgg ccagcccaag gccaacccca ccgtgaccct gttcccccca     360
tcttctgagg agctgcaagc caacaaggcc accctggtgt gcctgatctc tgacttctac     420
cctggcgctg tgacagtggc ctggaaggct gatggctctc ctgtgaaggc tggcgtggag     480
accaccaagc catctaagca gtctaacaac aagtatgctg cctcttctta cctgtctctg     540 accccctgagc agtggaagag ccaccggtct tactcttgcc aggtgaccca tgagggctct     600
acagtggaga agacagtggc ccccacagag tgctct                                636

<210> SEQ ID NO 6
<211> LENGTH: 1341
<212> TYPE: DNA
<213> ORGANISM: Homo Sapien

<400> SEQUENCE: 6
caggtgcaat tggtggaaag cggcggcggc ctggtgcaac cgggcggcag cctgcgtctg      60
agctgcgcgg cctccggatt taccttttct gatcattgga tgcattgggt cgccaagcc     120 cctgggaagg gtctcgagtg ggtgagctat atcgattatt atggtagcaa tacccattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtatgctt     300 tatggtttgga attatggtgt ttttgattat tggggccaag gcaccctggt gacggttagc     360
tcagcatcca ccaagggccc atccgtcttc cccctggcgc cctgctccag gagcacctcc     420
gagagcacag ccgccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgacct ccagcaactt tggcacgcag     600
acctacacct gcaacgtaga tcacaagccc agcaacacca aggtggacaa gacagttgag     660
cggaaatgct gcgtggagtg cccaccatgc ccagcacctc cagtggccgg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
```

```
ggcgtggagg tgcataatgc caagacaaag ccgcgggagg agcagttcaa cagcacgttc    900
cgtgtggtca gcgtcctcac cgtcctgcac caggactggc tgaacggcaa ggagtacaag    960
tgcaaggtct ccaacaaagg cctcccgtcc tccatcgaga aaccatctc caaaaccaaa    1020 gggcagcccc gagagccaca ggtgtacacc ctgcccccat cccgggagga gatgaccaag   1080
aaccaggtca gcctgacctg cctggtcaaa ggcttctacc ccagcgacat cgccgtggag   1140
tgggagagca tgggcagcc ggagaacaac tacaagacca cgcctcccat gctggactcc    1200
gacggctcct tcttcctcta cagcaagcta accgtggaca gagcaggtg gcagcagggg    1260 aatgtcttct catgctccgt gatgcatgag gctctgcaca ccactacac acagaagagc    1320 ctctccctgt ctcctggtaa a                                             1341
```

```
<210> SEQ ID NO 7
<211> LENGTH: 212
<212> TYPE: PRT
<213> ORGANISM: Homo Sapien

<400> SEQUENCE: 7
```

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Arg Asp Lys Tyr Val
            20                  25                  30

His Trp Tyr Gln Gln Lys Pro Gly Gln Ala Pro Val Val Ile Tyr
        35                  40                  45

Tyr Asp Thr Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ala Tyr Thr Arg Ser Ile Tyr Val
                85                  90                  95

Phe Gly Gly Gly Thr Lys Leu Thr Val Leu Gly Gln Pro Lys Ala Asn
            100                 105                 110

Pro Thr Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Gly Ser Pro Val Lys Ala Gly Val Glu
145                 150                 155                 160

Thr Thr Lys Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

```
<210> SEQ ID NO 8
<211> LENGTH: 447
<212> TYPE: PRT
<213> ORGANISM: Homo Sapien

<400> SEQUENCE: 8
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His

-continued

```
                    20                  25                  30
Trp Met His Trp Val Arg Gln Ala Pro Gly Lys Gly Leu Glu Trp Val
        35                  40                  45
Ser Tyr Ile Asp Tyr Tyr Gly Ser Asn Thr His Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Met Leu Tyr Gly Trp Asn Tyr Gly Val Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Thr Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445
```

<210> SEQ ID NO 9
<211> LENGTH: 645
<212> TYPE: DNA
<213> ORGANISM: Homo Sapien

<400> SEQUENCE: 9

```
gatatcgtgc tgacccagag cccggcgacc ctgagcctgt ctccgggcga acgtgcgacc      60
ctgagctgca gcgagcca gtctgttaat tctaattatc tggcttggta ccagcagaaa      120
ccaggtcaag caccgcgtct attaatttat ggtgcttctt ctcgtgcaac tggggtcccg      180
gcgcgtttta gcggctctgg atccggcacg gattttaccc tgaccattag cagcctggaa      240
cctgaagact ttgcggttta ttattgccag cagtggggtg atgttcctat tacctttggc      300
cagggtacga agttgaaat taaacgtacg gtggctgctc cgagcgtgtt tattttccg      360
ccgagcgatg aacaactgaa agcggcacg gcgagcgtgg tgtgcctgct gaacaacttt      420
tatccgcgtg aagcgaaagt tcagtggaaa gtagacaacg cgctgcaaag cggcaacagc      480
caggaaagcg tgaccgaaca ggatagcaaa gatagcacct attctctgag cagcacctg      540
accctgagca agcggatta tgaaaaacat aaagtgtatg cgtgcgaagt gacccatcaa      600
ggtctgagca gcccggtgac taaatctttt aatcgtggcg aggcc                     645
```

<210> SEQ ID NO 10
<211> LENGTH: 714
<212> TYPE: DNA
<213> ORGANISM: Homo Sapien

<400> SEQUENCE: 10

```
caggtgcaat tggtggaaag cggcggcggc ctggtgcaac cgggcggcag cctgcgtctg      60
agctgcgcgg cctccggatt tacctttct gattattata tgcattgggt cgccaagcc      120
cctgggaagg gtctcgagtg ggtgagcaat atctctggtt ctggtagcac tacctattat      180
gcggatagcg tgaaaggccg ttttaccatt tcacgtgata attcgaaaaa caccctgtat      240
ctgcaaatga acagcctgcg tgcggaagat acggccgtgt attattgcgc gcgtggtatg      300
tttgattttt ggggccaagg caccctggtg acggttagct cagcgtcgac caaaggtcca      360
agcgtgtttc cgctggctcc gagcagcaaa agcaccagcg gcggcacggc tgccctgggc      420
tgcctggtta agattatttt cccggaacca gtcaccgtga ctggaacag cggggcgctg      480
accagcggcg tgcataccct tccggcggtg ctgcaaagca gcggcctgta gcctgagc      540
agcgttgtga ccgtgccgag cagcagctta ggcactcaga cctatatttg caacgtgaac      600
cataaaccga gcaacaccaa agtggataaa aaagtggaac cgaaaagcga attcgagcag      660
aagctgatct ctgaggagga tctgaacggc gcgccgcacc atcatcacca tcac           714
```

<210> SEQ ID NO 11
<211> LENGTH: 215
<212> TYPE: PRT
<213> ORGANISM: Homo Sapien

<400> SEQUENCE: 11

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Ser Asn
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Val Pro Ala Arg Phe Ser
```

```
                50                  55                  60
Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Trp Gly Asp Val Pro
                 85                  90                  95

Ile Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Ala
                210                 215

<210> SEQ ID NO 12
<211> LENGTH: 237
<212> TYPE: PRT
<213> ORGANISM: Homo Sapien

<400> SEQUENCE: 12

Gln Val Gln Leu Val Glu Ser Gly Gly Gly Leu Val Gln Pro Gly Gly
 1                5                  10                  15

Ser Leu Arg Leu Ser Cys Ala Ala Ser Gly Phe Thr Phe Ser Asp Tyr
                 20                  25                  30

Tyr Met His Trp Val Arg Gln Ala Pro Gly Lys Gly Leu Glu Trp Val
                 35                  40                  45

Ser Asn Ile Ser Gly Ser Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Met Phe Asp Phe Trp Gly Gln Gly Thr Leu Val Thr Val Ser
                100                 105                 110

Ser Ala Ser Thr Lys Gly Pro Ser Val Phe Pro Leu Ala Pro Ser Ser
                115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
                195                 200                 205

Lys Lys Val Glu Pro Lys Ser Glu Phe Glu Gln Lys Leu Ile Ser Glu
```

```
              210                 215                 220
Glu Asp Leu Asn Gly Ala Pro His His His His His His
225                 230                 235

<210> SEQ ID NO 13
<211> LENGTH: 645
<212> TYPE: DNA
<213> ORGANISM: Homo Sapien

<400> SEQUENCE: 13
gatatcgtgc tgacccagag cccggcgacc ctgagcctgt ctccgggcga acgtgcgacc    60
ctgagctgca gagcgagcca gtctgttaat tctaattatc tggcttggta ccagcagaaa   120
ccaggtcaag caccgcgtct attaatttat ggtgcttctt ctcgtgcaac tggggtcccg   180
gcgcgtttta gcggctctgg atccggcacg gattttaccc tgaccattag cagcctggaa   240
cctgaagact ttgcggttta ttattgccag cagtggggtg atgttcctat tacctttggc   300
cagggtacga aagttgaaat taaacgtacg gtggctgcac atctgtcttc atcttcccg    360 ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag acagcacct acagcctcag cagcaccctg    540
acgctgagca agcagacta cgagaaacac aaagtctacg cctgcgaagt cacccatcag   600
ggcctgagct cgcccgtcac aaagagcttc aacaggggag agtgt                  645

<210> SEQ ID NO 14
<211> LENGTH: 1320
<212> TYPE: DNA
<213> ORGANISM: Homo Sapien

<400> SEQUENCE: 14
caggtgcaat tggtggaaag cggcggcggc ctggtgcaac cgggcggcag cctgcgtctg    60
agctgcgcgg cctccggatt tacctttcct gattattata tgcattgggt cgccaagcc   120 cctgggaagg gtctcgagtg ggtgagcaat atctctggtt ctggtagcac tacctattat   180
gcggatagcg tgaaaggccg ttttaccatt tcacgtgata attcgaaaaa cacccctgtat   240 ctgcaaatga acagcctgcg tgcggaagat acggccgtgt attattgcgc gcgtggtatg   300
tttgattttt ggggccaagg caccctggtg acggttagct cagcatccac caagggccca   360
tccgtcttcc ccctggcgcc ctgctccagg agcacctccg agagcacagc cgccctgggc   420
tgcctggtca aggactactt ccccgaaccg gtgacggtgt cgtggaactc aggcgccctg   480
accagcggcg tgcacacctt cccggctgtc ctacagtcct caggactcta ctccctcagc   540
agcgtggtga ccgtgacctc cagcaacttt ggcacgcaga cctacacctg caacgtagat   600
cacaagccca gcaacaccaa ggtggacaag acagttgagc ggaaatgctg cgtggagtgc   660
ccaccatgcc cagcacctcc agtggccgga ccatcagtct tcctgttccc cccaaaaccc   720
aaggacactc tcatgatctc ccggacccct gaggtcacgt gcgtggtggt ggacgtgagc   780
caggaagacc ccgaggtcca gttcaactgg tacgtggatg gcgtggaggt gcataatgcc   840
aagacaaagc cgcgggagga gcagttcaac agcacgttcc gtgtggtcag cgtcctcacc   900
gtcctgcacc aggactggct gaacggcaag gagtacaagt gcaaggtctc caacaaaggc   960
ctcccgtcct ccatcgagaa aaccatctcc aaaaccaaag ggcagccccg agagccacag  1020
gtgtacaccc tgcccccatc ccgggaggag atgaccaaga accaggtcag cctgacctgc  1080
ctggtcaaag gcttctaccc cagcgacatc gccgtggagt gggagagcaa tgggcagccg  1140
```

```
gagaacaact acaagaccac gcctcccatg ctggactccg acggctcctt cttcctctac   1200
agcaagctaa ccgtggacaa gagcaggtgg cagcagggga atgtcttctc atgctccgtg   1260
atgcatgagg ctctgcacaa ccactacaca cagaagagcc tctccctgtc tcctggtaaa   1320
```

<210> SEQ ID NO 15
<211> LENGTH: 215
<212> TYPE: PRT
<213> ORGANISM: Homo Sapien

<400> SEQUENCE: 15

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Asn Ser Asn
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Trp Gly Asp Val Pro
             85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 16
<211> LENGTH: 440
<212> TYPE: PRT
<213> ORGANISM: Homo Sapien

<400> SEQUENCE: 16

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Tyr Met His Trp Val Arg Gln Ala Pro Gly Lys Gly Leu Glu Trp Val
         35                  40                  45

Ser Asn Ile Ser Gly Ser Gly Ser Thr Thr Tyr Tyr Ala Asp Ser Val
     50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Met Phe Asp Phe Trp Gly Gln Gly Thr Leu Val Thr Val
            100                 105                 110

Ser Ser Ala Ser Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Thr Ser Ser Asn Phe Gly Thr
            180                 185                 190

Gln Thr Tyr Thr Cys Asn Val Asp His Lys Pro Ser Asn Thr Lys Val
            195                 200                 205

Asp Lys Thr Val Glu Arg Lys Cys Cys Val Glu Cys Pro Pro Cys Pro
210                 215                 220

Ala Pro Pro Val Ala Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Phe Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Thr Lys Gly Gln Pro
            325                 330                 335

Arg Glu Pro Gln Val Tyr Thr Leu Pro Pro Ser Arg Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Met Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
            420                 425                 430

Ser Leu Ser Leu Ser Pro Gly Lys
            435                 440
```